United States Patent
Johnson et al.

(10) Patent No.: US 10,106,183 B2
(45) Date of Patent: Oct. 23, 2018

(54) STABILIZER WHEEL ASSEMBLY AND METHODS OF USE

(71) Applicant: GLOBUS MEDICAL, INC., Audubon, PA (US)

(72) Inventors: Norbert Johnson, North Andover, MA (US); Timothy Moulton, Newport, RI (US); James Pelletier, Boston, MA (US); Kevin Zhang, Medford, MA (US); Jared Judson, Medford, MA (US); Gerd Schmieta, Boston, MA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 15/681,836

(22) Filed: Aug. 21, 2017

(65) Prior Publication Data

US 2017/0341668 A1 Nov. 30, 2017

Related U.S. Application Data

(63) Continuation of application No. 14/881,291, filed on Oct. 13, 2015, now Pat. No. 9,771,092.

(51) Int. Cl.
| | |
|---|---|
| *B62B 3/02* | (2006.01) |
| *A61B 34/00* | (2016.01) |
| *A61B 34/30* | (2016.01) |
| *A61B 50/13* | (2016.01) |
| *B62B 3/10* | (2006.01) |
| *B62B 3/00* | (2006.01) |

(52) U.S. Cl.
CPC .............. *B62B 3/022* (2013.01); *A61B 34/25* (2016.02); *A61B 34/30* (2016.02); *A61B 50/13* (2016.02); *B62B 3/008* (2013.01); *B62B 3/10* (2013.01); *B62B 2202/48* (2013.01); *B62B 2202/56* (2013.01); *B62B 2301/04* (2013.01)

(58) Field of Classification Search
CPC ............ B62B 2202/56; B62B 2301/04; B62B 5/0033; B62B 5/0036; B62B 5/0043; A61B 50/13; A61B 34/25
See application file for complete search history.

(56) References Cited

U.S. PATENT DOCUMENTS

| | | | |
|---|---|---|---|
| 5,184,601 A | 2/1993 | Putman | |
| 5,794,639 A | 8/1998 | Einbinder | |
| 8,365,353 B2 * | 2/2013 | Block | B60B 33/0007 16/35 R |
| 9,492,341 B2 * | 11/2016 | Huster | A61B 5/1115 |
| 2007/0114079 A1 | 5/2007 | Chao | |
| 2014/0059768 A1 | 3/2014 | Lemire et al. | |
| 2014/0275955 A1 | 9/2014 | Crawford et al. | |

* cited by examiner

*Primary Examiner* — Erez Gurari

(57) ABSTRACT

Included is a stabilizer wheel assembly that may assist in stabilizing a medical device during a medical procedure. A medical device may comprise a body; and a plurality of stabilizer wheel assemblies coupled to the body, wherein the stabilizer wheel assemblies each comprise a motor assembly and a stabilization leg, wherein the motor assembly is configured to drive the stabilization leg onto a contact surface to stabilize the body.

18 Claims, 6 Drawing Sheets

STABILIZER WHEEL ASSEMBLY AND METHODS OF USE

CROSS REFERENCE TO RELATED APPLICATIONS

This application is a continuation of U.S. patent application Ser. No. 14/881,291, filed on Oct. 13, 2015 (published as U.S. Patent Publication No. 2017-0101118), the contents of which is hereby incorporated by reference in its entirety for all purposes.

FIELD OF THE INVENTION

Embodiments are directed to a stabilizer wheel assembly and, more particularly, a stabilizer wheel assembly that may assist in stabilizing a medical device during a medical procedure.

BACKGROUND

Various medical devices may need to be stabilized before a medical procedure. However, most flooring may not be flat throughout the entire surface area. Often there may be high and low areas within flooring that may prevent a medical device from remaining stable. A stabilized medical device may be essential for many medical procedures. Even the slightest movement of the medical device may lead to catastrophic harm of a patient. Conventionally, medical personnel may place stops and/or wedges to help stabilize the medical device. This manual process, even if done correctly, may allow movement of the medical device during a medical procedure. The success of a medical procedure may largely depend on the stability of the medical device.

Consequently, there is a need for a stabilizer wheel assembly that may be used to stabilize a medical device. The ability to perform a medical procedure on a patient with a stable device may greatly diminish the possibility of harming a patient during the medical procedure. The application of a stabilizer wheel assembly and the techniques used with the stabilizer wheel assembly may enhance the overall medical procedure and the results of the procedure.

SUMMARY

An embodiment may include a medical device, wherein the medical device may comprise a body; and a plurality of stabilizer wheel assemblies coupled to the body, wherein the stabilizer wheel assemblies each comprise a motor assembly and a stabilization leg, wherein the motor assembly is configured to drive the stabilization leg onto a contact surface to stabilize the body.

Another embodiment may include a method of stabilizing a medical device, wherein the method may comprise positioning the medical device for a medical procedure; activating a plurality of stabilizer wheel assemblies of the medical device to lower a stabilization leg from each of the stabilizer wheel assemblies; and driving the stabilization leg of each of the stabilizer wheel assemblies onto a contact surface.

BRIEF DESCRIPTION OF THE DRAWINGS

For a detailed description of the preferred embodiments of the invention, reference will now be made to the accompanying drawings in which.

DETAILED DESCRIPTION

Embodiments relate generally to a stabilizer wheel assembly for use with medical devices. More particularly, embodiments relate to a motor assembly and stabilizing leg assembly mounted to a caster, which may be used to stabilize medical devices. A stabilizer wheel assembly may comprise a caster, a stem, a motor assembly, a bumper, and a stabilizing leg assembly. In embodiments, a medical device may have a plurality of stabilizer wheel assemblies. The stabilizer wheel assemblies may allow personnel to maneuver medical devices to a medical procedure with ease. The medical devices may then be positioned to help facilitate the medical procedure. In many cases, the floor upon which the medical devices may be disposed may be uneven. This may lead to sudden movement of medical devices during a medical procedure. The stabilizer wheel assembly may be used to stabilize medical devices and prevent sudden movements. In embodiments a stabilizing leg assembly and motor assembly may be used to drive a stabilization leg onto a contact surface. The stabilization leg may stabilize the medical device and help prevent sudden movements of the medical device.

Figure 1:
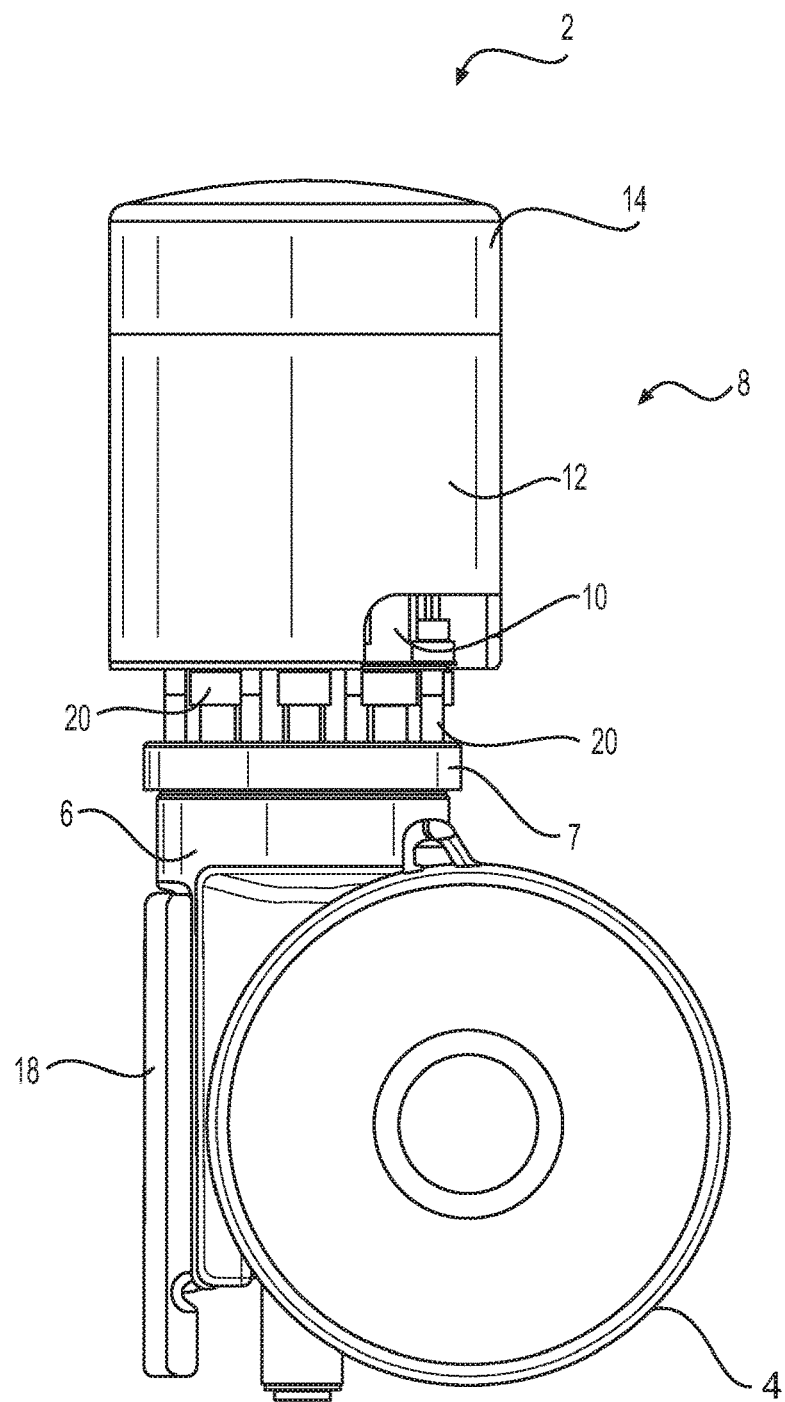
FIG. 1 illustrates an embodiment of a stabilizer wheel assembly.

FIG. 1 illustrates an embodiment of a stabilizer wheel assembly 2. Stabilizer wheel assembly 2 may comprise a caster 4, a stem 6, a motor assembly 8, attachment means 20, and a bumper 18. Caster 4 may be a structure upon which the rest of stabilizer wheel assembly 2 may be disposed. In embodiments, caster 4 may comprise a single, double, and/or compound wheels. Caster 4 may be any type of rigid, swivel, industrial, and/or braking and locking wheels. Caster 4 may comprise any material suitable for supporting and facilitating movement of a medical device. Suitable material may be, but is not limited to, rubber, plastic, nylon, aluminum, stainless steel, and/or any combination thereof. Additionally, caster 4 may be of any suitable diameter and width. A suitable diameter may be about one inch to about six inches, about two inches to about four inches, or about three inches to about six inches. A suitable width may be about a quarter inch to about two inches, about half an inch to about an inch, or about an inch to about two inches. In embodiments, caster 4 may rotate three hundred and sixty degrees around stem 6. Stem 6 may provide an additional structure which other components of stabilizer wheel assembly 2 may be disposed.

As illustrated in FIG. 1, stem 6 may be a structure in which caster 4, motor assembly 8, and bumper 18 are disposed. In embodiments, stem 6 may be a hollow tube with at least one flanged surface 7, best illustrated in FIG. 2. Referring to FIG. 1, caster 4 may attach to stem 6 through a tapered roller bearing and a coaxial roller bearing. A retaining ring captures caster 4 and prevents the caster housing from falling off the stem. Additionally, caster 4 may be disposed on stem 6 at any suitable location. In embodiments, caster 4 may be disposed about an edge and/or about the bottom of stem 6. Stem 6 may further house stabilizing leg assembly 22, as disclosed below. In embodiments, stem 6 may be made of any suitable material in which to support a medical device. Suitable material may be, but is not limited to, rubber, plastic, nylon, aluminum, stainless steel, and/or any combination thereof. Stem 6 may be any suitable length to support stabilizer wheel assembly 2. A suitable length may be about one inch to about six inches, about two inches to about four inches, or about three inches to about five inches. Additionally, stem 6 may have any suitable inside diameter in which to dispose stabilizing leg assembly 22. A suitable diameter may be about half an inch to about two inches, about three quarters of an inch to about an inch and a half, or about one inch to about two inches. Stabilizing leg assembly 22 may be powered by motor assembly 8. In embodiments, motor assembly 8 may be disposed upon stem 6.

Figure 2:
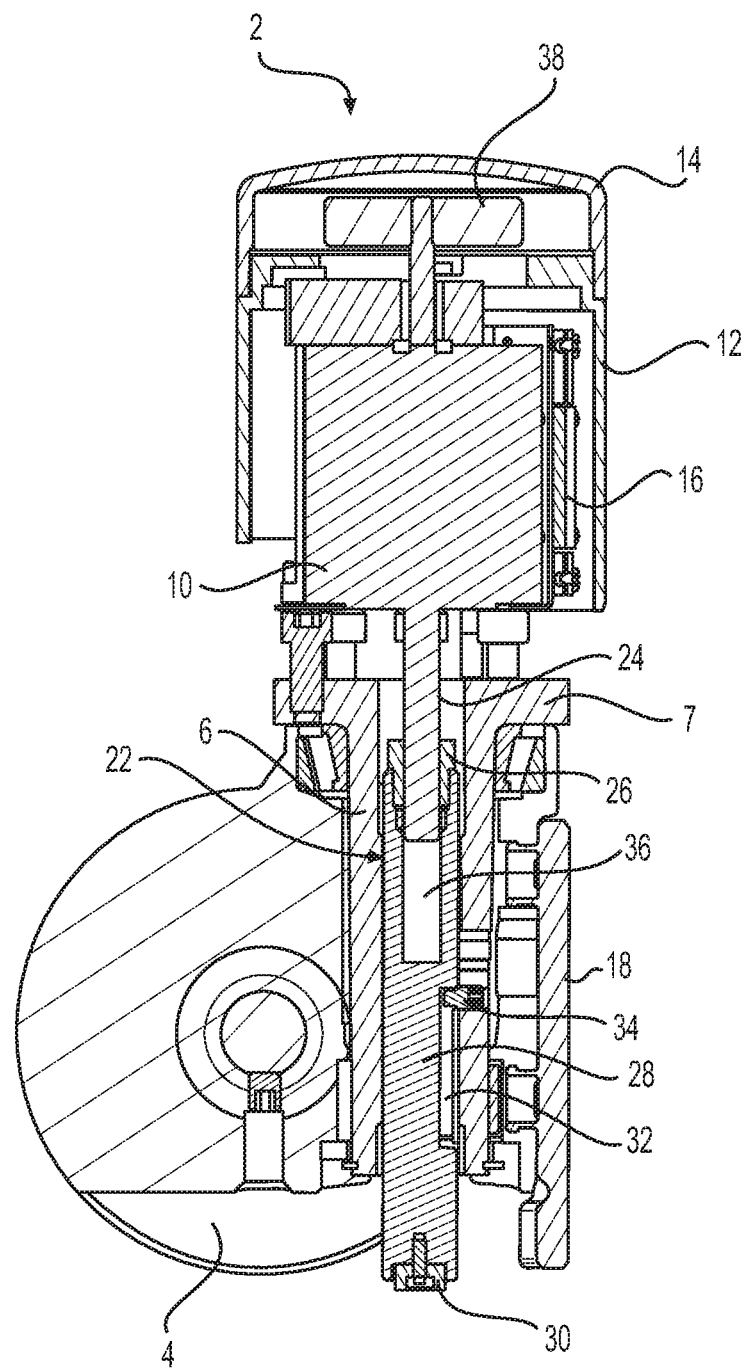
FIG. 2 illustrates a cutaway view of an embodiment of a stabilizer wheel assembly.
Figure 3:
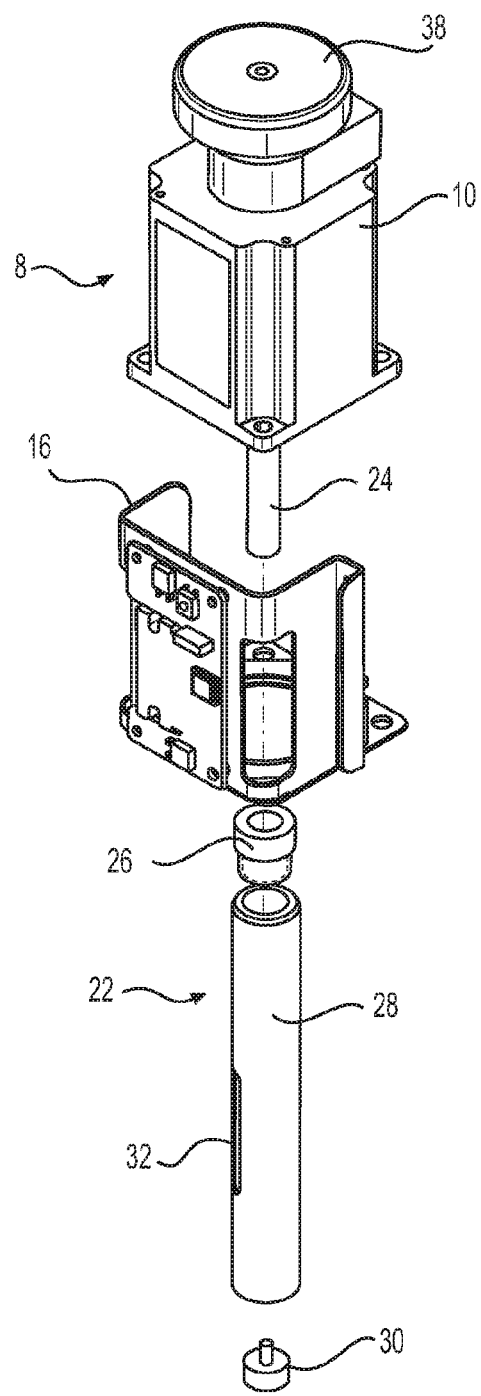
FIG. 3 illustrates an embodiment of a motor and a stabilizing leg assembly.

Referring to FIG. 3, motor assembly 8 may be disposed about the top of stem 6. Additionally, motor assembly 8 may be disposed upon stem 6 at any suitable location. In embodiments, motor assembly may be disposed about an edge and/or along the bottom of stem 6. Motor assembly 8 may attach to stem 6 by any suitable means. Suitable means may be, but are not limited to, nuts and bolts, screws, adhesive, and/or any combination thereof. As illustrated in FIGS. 1-3, motor assembly 8 may comprise a motor 10, a motor cover 12, a motor cap 14, and a motor bracket 16. Motor 10 may be a structure upon which motor cover 12, motor cap 14, and motor bracket 16 may be disposed. Additionally, motor 10 may attach about the top and/or about and edge of stem 6. In embodiments, motor 10 may be any type of suitable motor 10. A suitable motor 10 may be, but is not limited to, a permanent magnet stepper, a hybrid synchronous stepper, a variable reluctance stepper, a lavet type stepping motor, a brushed servo motor, and/or a brushless servo motor. Additionally, motor 10 may comprise a unipolar or bipolar stepper motor. In embodiments, motor 10 may attach to a motor bracket 16. Attachment means 20, as illustrated in FIGS. 1-3, may attach motor 10, motor bracket 16, and motor assembly 8 to stem 6. Attachment means 20 may be, but are not limited to, nuts and bolts, screws, press fittings, adhesive, and/or any combination thereof. In embodiments, attachment means 20 may further connect motor cover 12 to stem 6. There may be a plurality of attachment means 20 disposed about the top of stem 6.

Motor bracket 16, as illustrated in FIGS. 2 and 3, may be used to stabilize motor 10 and may protect motor 10 from outside forces. In embodiments, motor bracket 16 may comprise any suitable material to firmly hold and protect motor 10. Suitable material may be, but is not limited to, rubber, plastic, nylon, aluminum, stainless steel, and/or any combination thereof. Additionally, best illustrated in FIG. 3, motor bracket 16 may be used as an attachment point for communication circuitry, which may allow motor 10 to communicate with robot system 42 (discussed below on FIG. 6). In embodiments, motor 10 and motor bracket 16 may attach to stem 6 through attachment means 20. Motor bracket 16 may be disposed about any suitable location of motor 10. Specifically, motor bracket 16 may be disposed below, above, or about a side of motor 10. In embodiments, motor bracket 16 may be disposed between stem 6 and motor 10, which may secure motor bracket 16 in place. Motor bracket 16 may attach to stem 6 and/or motor 10 by any suitable means. Suitable means may be, but are not limited to, nuts and bolts, screws, adhesive, press fittings, and/or any combination thereof. In embodiments, motor bracket 16 and motor 10 may be enclosed by motor cover 12 and motor cap 14.

As illustrated in FIGS. 1 and 2, motor cover 12 and motor cap 14 may protect motor 10 from foreign objects and outside forces. Both motor cover 12 and motor cap 14 may comprise any suitable material which may protect motor 10 from foreign objects and outside forces. Suitable material may be, but is not limited to, rubber, plastic, nylon, aluminum, stainless steel, and/or any combination thereof. In embodiments, motor cap 14 may attach to motor cover 12 by any suitable means. Suitable means may be, but are not limited to, snap fittings, threaded fitting, adhesive, nuts and bolts, screws, O-rings, and/or any combination thereof. Motor cover 12 may be any suitable shape. A suitable shape may be, but is not limited to, circular, triangular, square, rectangular, polyhedral, and/or any combination thereof. Best illustrated in FIG. 4, motor cover 12 may be disposed at the top of motor 10. Additionally, motor cover 10 may be disposed below or at about any edge of motor 10. In embodiments, motor cover 10 may partially enclose components of motor assembly 8. Motor cap 14 may be disposed on top of motor cover 12 and/or motor 10, which may partially enclose components of motor assembly 8. In embodiments, motor cap 14 may attach to motor cover 12 or motor 10 by any suitable means. Suitable means may be, but are not limited to, nuts and bolts, screws, adhesive, press fitting, O-ring, and/or any combination thereof. Motor cover 12 may be any suitable shape. A suitable shape may be, but is not limited to, circular, triangular, square, rectangular, polyhedral, and/or any combination thereof. Motor cover 12 and motor cap 14 may protect motor assembly 8. Stabilizer wheel assembly may further be protected from outside forces by bumper 18.

Bumper 18, as illustrated in FIGS. 1 and 2, may protect stem 6 from foreign objects, outside forces, and may prevent cables and/or other cords from going under stem 6. Bumper 18 may be made of any suitable material to absorb impacts from foreign objects and prevent objects from sliding under stem 6. Suitable material may be, but is not limited to, rubber, plastic, nylon, polyurethane, and/or any combination thereof. In embodiments bumper 18 may snap fit into the caster or by any suitable means. Suitable means may be, but are not limited to, snap fittings, adhesive, nuts and bolts, screws, and/or any combination thereof. Bumper 18 may be any suitable shape. A suitable shape may be, but is not limited to, circular, triangular, square, rectangular, polyhedral, and/or any combination thereof. In embodiments, bumper 18 may be disposed opposite casters 4. Additionally, bumper 18 may be disposed about any edge and a plurality of bumpers 18 may be disposed along any number of edges of stem 6. Any item under stem 6 may prevent stabilizing leg assembly 22 from operating correctly, which may prevent stabilization of a medical device. Removing objects from stem 6 may allow for stabilizing leg assembly 22 to firmly stabilize a medical device. Bumper 18 may be any suitable length in which to prevent objects from moving below stem 6. In embodiments, best illustrated in FIG. 1, bumper 18 may almost touch the same contact surface as caster 4. This additional length may facilitate in pushing and/or removing cables and other objects from the path of caster 4 and stem 6. Removing objects from beneath stabilizing leg assembly 22 may allow properly stabilize medical robot system 42, discussed below.

As illustrated in FIGS. 2 and 3, stabilizing leg assembly 22 may be used to stabilize a medical device. Stabilizing leg assembly 22 may comprise a lead screw 24, a nut 26, a stabilizing leg 28, a foot 30, a channel 32, and a set screw 34. To prevent failure of stabilizing leg assembly 22 under weight of a medical device, stabilizing leg assembly may be made of any suitable material to support the weight of the medical device. Suitable material may be, but is not limited to, rubber, plastic, nylon, aluminum, stainless steel, and/or any combination thereof. In embodiments, lead screw 24 may be directly disposed within motor 10. Lead screw 24 may be disposed below and/or within motor 10. Lead screw 24 may attach to motor 10 by any suitable means. Suitable means may be, but are not limited to, nuts and bolts, screws, adhesive, press fittings, and/or any combination thereof. In embodiments, lead screw 24 may operate as a transmission shaft, which may rotate in any direction, distributing rotational force to an attached device. Additionally, lead screw 24 may rotate as fast and/or as slow as motor 10 may allow. Rotation of lead screw 24 may remove stabilizing leg 28 from a contact surface and may dispose stabilizing leg 28 onto the contact surface. In embodiments, lead screw 24 may comprise low pitch threading. Low pitch threading may require more revolutions of lead screw 24 in order to move stabilizing leg 28 up and/or down. Low pitch threading as well as high friction or inefficient force transmission may prevent lead screw 24 from moving and/or rotating under the weight of a medical device, which may prevent stabilizing leg 28 from collapsing into stabilizer wheel assembly 2. The rotational force, for creating up and down movement of stabilizing leg 28, may be transferred from lead screw 24 to stabilizing leg 28 through nut 26. Nut 26 may be disposed upon lead screw 24 and stabilizing leg 28.

As illustrated in FIGS. 2 and 3, nut 26 may attach to stabilizing leg 28 by any suitable means. Suitable means may be, but are not limited to, weld, adhesive, forming, nuts and bolts, screws, and/or any combination thereof. Nut 26 may be disposed at an end of stabilizing leg 28 opposite foot 30 and closest to motor 10. In embodiments, the rotation of lead screw 24 may move nut 26, and in turn stabilizing leg 28, up and down. As nut 26 and stabilizing leg 28 traverse lead screw 24, lead screw 24 may enter into a pocket 36 of stabilizing leg 28, best illustrated in FIG. 2. Pocket 36 may allow stabilizing leg 28 and nut 26 to traverse lead screw 24 without binding and/or collapsing lead screw 24. In embodiments, pocket 36 may be a hollow section within stabilizing leg 28. Pocket 36 may traverse the length of stabilizing leg 28 and/or be located at an end of stabilizing leg 28 opposite foot 30. Pocket 36 may allow for stabilizing leg 28 to rotate, be risen, and/or lowered without harming stabilizing leg 28. In embodiments, to prevent stabilizing leg 28 from rotating with lead screw 24, a channel 32 and set screw 34 may be used to prevent rotational motion of stabilizing leg 28.

Figure 4:
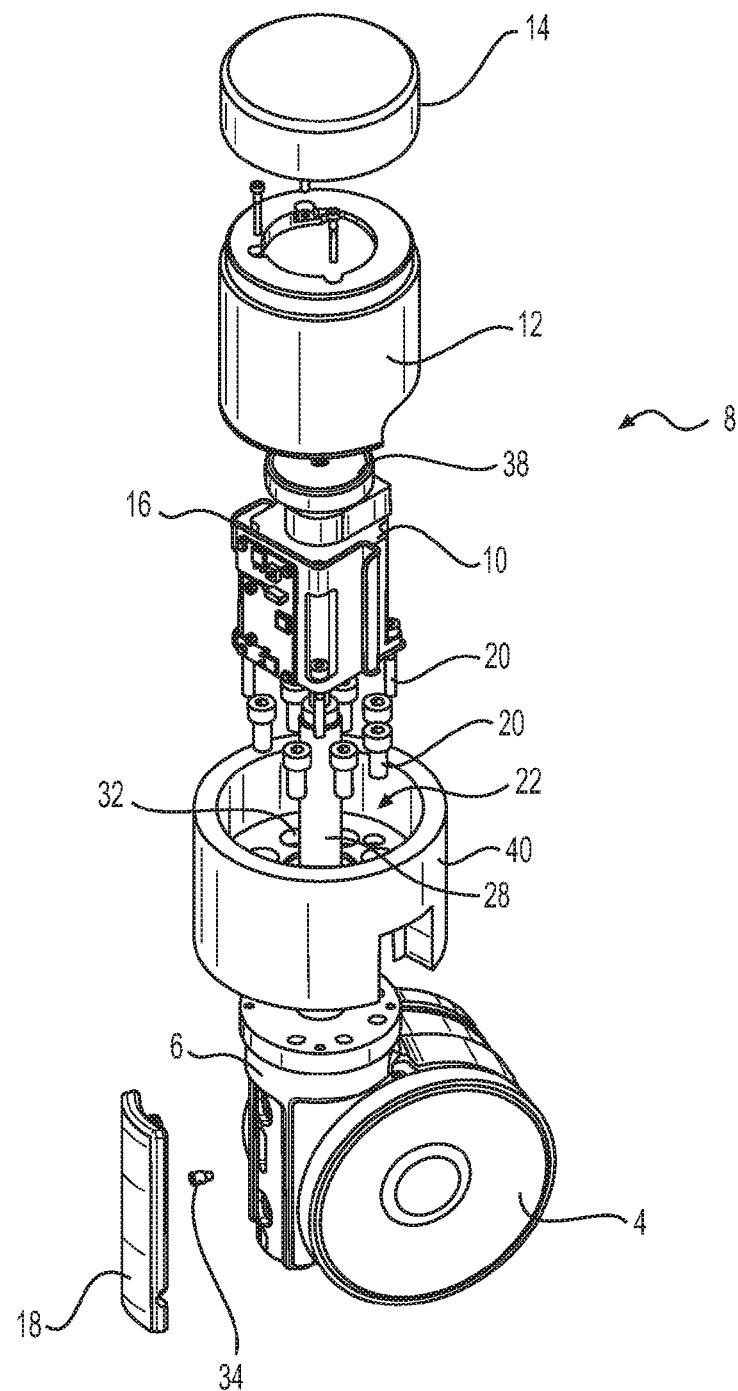
FIG. 4 illustrates an exploded view of an embodiment of a stabilizer wheel assembly.

Best illustrated in FIGS. 2 and 3, channel 32 may be a vertical cut-out along stabilizing leg 28. Channel 32 may be disposed along any edge of stabilizing leg 28. Additionally, channel 32 may be disposed on an edge of stabilizing leg 28 closest to bumper 18 and opposite caster 4. In embodiments, channel 32 may run the length of movement allowed by stabilizer motor 10. In additional embodiments, channel 32 may run the entire length of stabilizing leg 28. Referring to FIGS. 2 and 4, a set screw 34 may protrude through stem 6 and into channel 32. In embodiments, set screw 34 may be disposed along any edge of stem 6. Specifically, set screw 34 may be disposed at an edge opposite caster 4 and closest to bumper 18. Set screw 34 may attach to stem 6 by any suitable means, suitable means may be, but are not limited to, a snap fitting, threaded fitting, nuts and bolts, and/or any combination thereof. Protruding into channel 32 from stem 6, set screw 34 may prevent the rotational movement, in any direction, of stabilizing leg 28. This may allow stabilizing leg 28 to move up and/or down and not rotate with lead screw 24. In embodiments, stabilizing leg 28 may contact any surface. A foot 30 may act as a buffer between stabilizing leg 28 and the contact surface.

Foot 30, as illustrated in FIGS. 2 and 3 may act as a medium between stabilizing leg 28 and a contact surface. Foot 30 may comprise any suitable material in which to prevent damage and movement of stabilizing leg 28. Suitable material may be, but is not limited to, rubber, plastic, nylon, polyurethane, and/or any combination thereof. In embodiments, foot 30 may be any suitable shape. A suitable shape may be, but is not limited to circular, triangular, oval, square, rectangular, polyhedral, and/or any combination thereof. Additionally, foot 30 may attach to stabilizing leg 28 by any suitable means. Suitable means may be, but are not limited to, nuts and bolts, screws, adhesive, press fitting, and/or any combination thereof. Foot 30 may be disposed at an end of stabilizing leg 28 opposite nut 26 and farthest away from motor 10. In embodiments, foot 30 may increase the friction between stabilizing leg 28 and a contact surface, which may further help prevent movement of stabilizing leg 28. In embodiments, the force exerted upon a contact surface by stabilizing leg 28 and foot 30 may be controlled by medical robot system 42.

Figure 5:
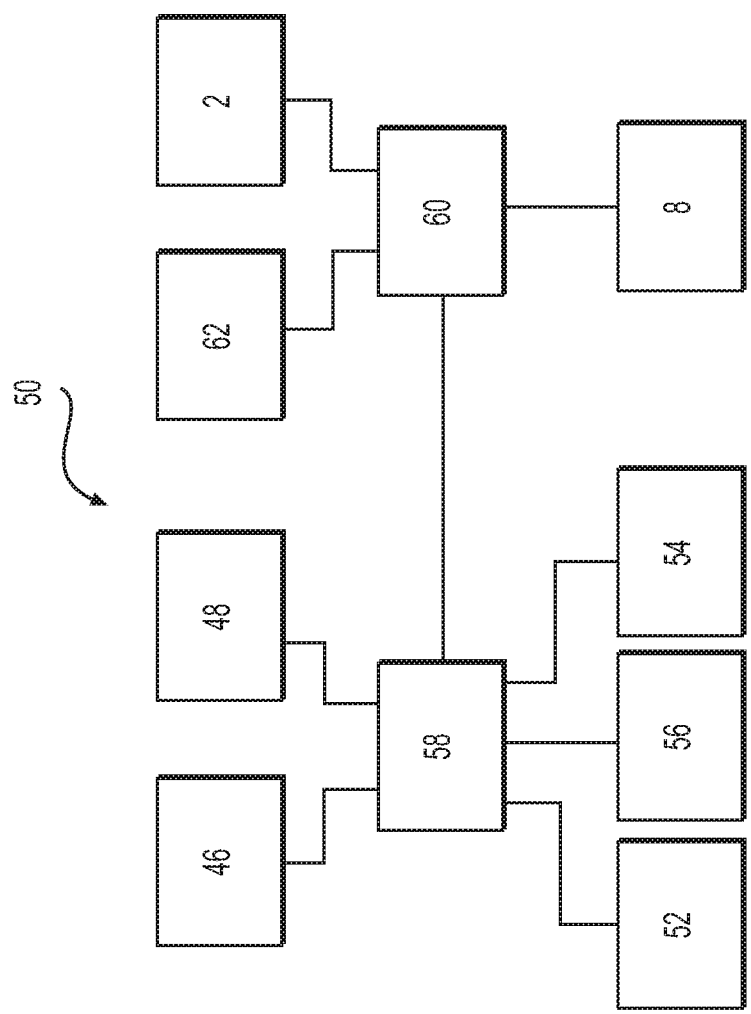
FIG. 5 illustrates an embodiment of a computer infrastructure.

FIG. 5 illustrates a schematic of software architecture 50 which may be used within medical robot system 42 to communicate with stabilizer wheel assembly 2. Software architecture 50 may be used to lower and raise stabilizing leg 28. Additionally, software architecture 50 may allow an operator to manipulate medical robot system 42 based upon commands given from an operator. In examples, operator commands may comprise Picture Archival and Communication Systems (PACS) 52, USB Devices 90, and commands from a wireless device 56. These operator commands may be received and transferred throughout medical robot system 42 by a computer processor 58. Computer processor 58 may be able to receive all commands and manipulate medical robot system 42 accordingly. In examples, computer processor 58 may be able to control and identify the location of individual parts that comprise medical robot system 42. Communicating with tool assembly 46 and display assembly 48, discussed below, computer processor 58 may be able to assist medical personnel during a medical procedure. Additionally, computer processor 58 may be able to use commands from display assembly 48 to alter the positions of tool assembly 46. Computer processor 58 may use firmware 60 to issue commands and process signals. Firmware 60 may comprise commands that are hardwired to medical robot system 42. For example, computer processor 58 may communicate with stabilizer wheel assembly 2, and platform interface 62. Platform interface 62 may be a series of hardwired button commands that directly control medical robot system 42. Button commands are not limited to but may comprise functions that may move lower and rise stabilization legs 28. Additionally, computer processor 92 may process and distribute all operator commends from display assembly 48 to lower and rise stabilization legs 28.

To stabilize a medical device, computer processor 58 disposed within the medical robot system 42 may be used to communicate with stabilizer wheel assembly 2 to exert a pre-determined amount of force through stabilizing leg 28 to a contact surface. Motor 10 may use firmware 60 to interface with computer processor 58 disposed within medical robot system 42. Suitable firmware 60 may be, but is not limited to I2C and SPI. In embodiments, disposing stabilizing leg 28 onto a contact surface may be broken down into two states, a ground state and a lifting state. These states may help stabilize the medical device in a controlled manner.

In embodiments, the ground state may dispose stabilizing leg 28 and foot 30 onto a contact surface without applying force upon the contact surface. This may be accomplished by driving motor 10 at a low current, about 0.01 Amps to about 1.2 Amps, and monitoring for two encoder-based stop conditions. The first stop condition may be measuring instantaneous speed along an encoder frequency. A peak width of an encoder channel may be chosen as a proxy for frequency as the base line. With low torque, a certain empirically determined peak width may be encountered while stabilizing leg 28 may be moving with no resistance. Resistance may produce a consecutive number of peak widths that may be higher than the original base line, which may satisfy the first stop condition. The second stop condition may comprise of reading a moving average of peak counts at 100 ms, which may simply be a measurement of displacement over time. If the value falls below a quarter percent of the empirically determined "no load" average displacement, the second stop condition is satisfied. Both conditions may be satisfied simultaneously and/or separately, but both conditions must be met to complete the ground state. Satisfying the ground state, the second lift state may then begin. During the lift state, a current of about 2.5 Amps to about 4 Amps may be applied to the motor. The second lift state may only measure the encoder count of lead screw 24 revolutions. Meeting a predetermined count or a timeout condition, the second lift state may end. The second lifting state may be based on a prescribed displacement of stabilizing leg 28 and not force and/or torque. Additionally, the onboard computer, disposed on the medical device, may use states to retract stabilizing leg 28 from a contact surface. The system just drives the stabilizers up into the caster. In embodiments, stabilizing leg 28 may move manually upon activation of a manual override switch 38.

As illustrated in FIGS. 2 and 3, a manual override switch 38 may be disposed about the top and/or about an edge of motor 10. In embodiments, override switch 38 may attach to lead screw 24. In the event medical robot system 42 loses power, medical personnel may need to retract stabilizing leg 28 and foot 30 from the contact surface. A loss of power may prevent motor 10 from retracting stabilizing leg 28. Manual override switch 38 may be manually rotated to retract and/or lower stabilizing leg 28. In embodiments, manual override switch 38 may be made of any suitable material to facilitate rotation of lead screw 24. Suitable material may be, but is not limited to, rubber, plastic, nylon, aluminum, stainless steel, and/or any combination thereof. Manual override switch 38 may be any suitable shape. A suitable shape may be, but is not limited to circular, oval, square, triangular, rectangular, polyhedral, and/or any combination thereof. Rotation of manual override switch 38 may rotate lead screw 24 and in turn move stabilizing leg 28 up and down. This may allow medical personnel to move the medical device without power, even when stabilizing leg 28 is activated. Additionally, manual override switch 38 may be rotated in an opposite direction, which may lower stabilizing leg 28 on to a contact surface. In embodiments, manual override switch 38 may be accessed by removing motor cap 14. Motor assembly 2 may be disposed at any suitable location within medical robot device 42, which may allow access to manual override switch 38.

As illustrated in FIG. 4, a medical device attachment 40 may be attach to stabilizer wheel assembly 2 between stem 6 and motor assembly 8 through attachment devices 20. Medical device attachment 40 may transfer the weight of a medical device to stabilizer wheel assembly 2. In embodiments, medical device attachment 40 may also help protect stabilizer wheel assembly 2 from foreign objects and outside forces. Medical device attachment 40 may be made of any suitable material to structurally support the medical device and protect stabilizer wheel assembly 2 form foreign objects and outside forces. Suitable material may be, but is not limited to, rubber, plastic, nylon, aluminum, stainless steel, and/or any combination thereof. In embodiments, medical device attachment 40 may have any suitable geometry in which to properly attach to a medical device. A suitable geometry may be circular, square, triangular, polyhedral, oval, and/or any combination thereof. Medical device attachment 40 may be used to attach any number of stabilizer wheel assemblies to medical robot system 42.

Figure 6:
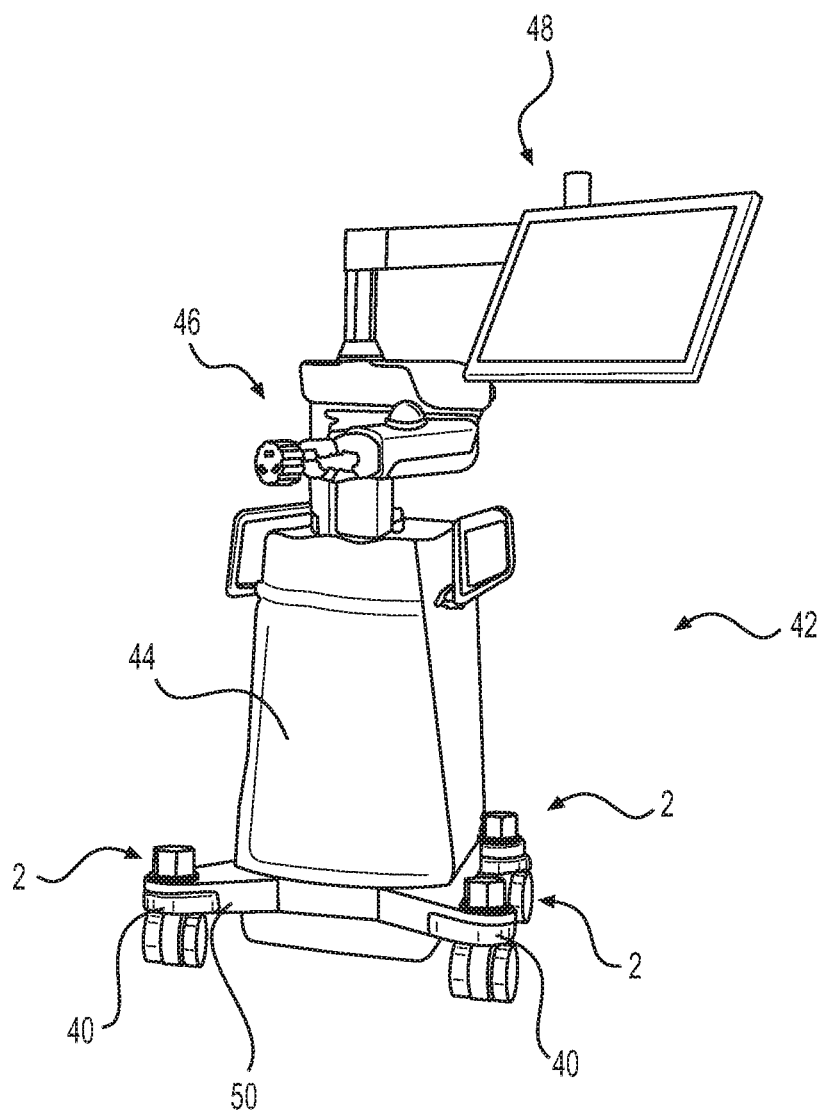
FIG. 6 illustrates and embodiment of a medical robot system.

Referring now to FIG. 6, a medical robot system 42 is illustrated in accordance with embodiments of the present invention. In the illustrated embodiment, the medical robot system comprises body 44, tool assembly 46, display assembly 48, and base 50. In embodiments, base 50 may provide a structure upon which stabilizer wheel assembly 2 and body 44 may be disposed. Stabilizer wheel assembly 2 may attach to base 50 through medical device attachments 40. Medical device attachments 40 may connect to base 50 by any suitable means. Suitable means may be, but are not limited to, nuts and bolts, screws, adhesive, press fittings, and/or any combination thereof. Additionally, there may be any suitable number of stabilizer wheel assemblies 2 to support and provide movement to base 50. In the illustrated, four stabilizer wheel assemblies 2 are shown arranged around the periphery of base. In embodiments, body 44 may be disposed on top of base 50. Body 44 may provide structure to medical robot system 42. Additionally, tool assembly 46 and display assembly 48 may be disposed at any suitable location on body 44. Tool assembly 46 may be disposed on top, about an edge, or about a side of body 44. Specifically, tool assembly 46 maybe disposed about the center of the top of base 44. Without limitation, tool assembly 46 may be configured to hold a surgical tool in a medical procedure. In embodiments, display assembly 48 may be disposed on top, about an edge, or about a side of body 44 or tool assembly 46. Specifically, display assembly 48 maybe disposed on top of tool assembly 46. In embodiments, body 4 may further house electronics, not illustrated, which may control medical robot system 42. It should be understood that medical robot system 42 illustrated on FIG. 6 is merely illustrative and the stabilizer wheel assemblies 2 may be used for stabilization of any of a variety of different medical robot systems.

To perform a medical procedure, medical robot system 42 may be moved from storage to a medical procedure room using stabilizer wheel assemblies 2. Stabilizer wheel assemblies 2 may allow medical personnel to maneuver medical robot system 42 around corners, through doors, through hallways, and elevators. Additionally, stabilizer wheel assemblies 2 may move medical robot system 42 in any direction and may allow for medical robot system 42 to rotate. After being positioned for a medical procedure, stabilizer wheel assemblies 2 may be activated using on board computers and circuitry housed in body 44. Display assembly 48 may provide an interface in which medical personnel may activate and control stabilizer wheel assemblies 2. Stabilizing leg 28 may be disposed to contact the surface below stabilizer wheel assemblies 2. As described above, a designated amount of force may be applied through stabilizing leg 28 to the contact surface. Applying an equal amount of force at each stabilizer wheel assembly 2 may create a stable platform, which may prevent medical robot system 42 from moving during a medical procedure. When medical robot system 42 may need to be moved after being activated, medical personnel may retract stabilizing leg 28 from the contact surface using display assembly 48 and/or manual override switch 38. Medical robot system 42 may then be maneuvered to any location for storage and/or further use.

Although the present invention and its advantages have been described in detail, it should be understood that various changes, substitutions and alterations may be made herein without departing from the spirit and scope of the invention as defined by the appended claims.

What is claimed is:

1. A medical robot system comprising:
   a body;
   a computer processor disposed within the body;
   a tool assembly attached to the body;
   a display assembly attached to the body;
   a base attached to the body; and
   at least one stabilizer wheel assembly disposed on the base,
   wherein each stabilizer wheel assembly comprises a motor and a stabilizer leg, and
   wherein the computer processor is configured to receive one or more commands from a platform interface to move each stabilizer leg by controlling each motor
   wherein each stabilizer wheel assembly comprises a foot attached to an end of the corresponding stabilization leg opposite a nut.

2. The medical device of claim 1, wherein the computer processor is configured to drive each stabilization leg into a contact surface until each stabilization leg exerts a predetermined force on the contact surface.

3. The medical device of claim 2, wherein each stabilizer wheel assembly further comprises a caster.

4. The medical device of claim 3, wherein each stabilizer wheel assembly further comprises a stem, wherein the corresponding caster rotates three hundred and sixty degrees around each stem.

5. The medical device of claim 4, wherein each motor is connected to a top of the corresponding stem.

6. The medical device of claim 5, wherein each stabilization leg is configured to extend through the corresponding caster to the contact surface.

7. The medical device of claim 1, wherein each stabilizer wheel assembly further comprises a motor cover that encloses each motor, a motor cap disposed on top of each motor, and a motor bracket that supports each motor.

8. The medical device of claim 1, wherein each foot increases the friction between the corresponding stabilization leg and a contact surface.

9. The medical device of claim 8, wherein each stabilizer wheel assembly further comprises a caster and a set screw is disposed on a side of the caster.

10. The medical device of claim 9, wherein the set screw of each stabilizer wheel assembly is secured into a corresponding channel to prevent the corresponding stabilization leg from rotating.

11. The medical device of claim 1, wherein each stabilizer wheel assembly further comprises a bumper.

12. A medical robot system comprising:
    a body;
    a stabilizer wheel assembly coupled to the body, wherein the stabilizer wheel assembly comprises a motor assembly and stabilization leg, wherein the motor assembly is configured to drive the stabilization leg onto a contact surface to stabilize the body; and
    a computer processor disposed within the body, wherein the computer processor is configured to receive one or more commands from a platform interface to move each stabilizer leg by controlling each motor
    wherein the stabilizer wheel assembly comprises a foot attached to an end of the stabilization leg opposite a nut.

13. The medical device of claim 12, wherein the computer processor is configured to drive the stabilization leg into the contact surface until the stabilization leg exerts a predetermined force on the contact surface.

14. The medical device of claim 13, wherein the stabilizer wheel assembly further comprises a caster.

15. The medical device of claim 14, wherein the stabilizer wheel assembly further comprises a stem, wherein the caster rotates three hundred and sixty degrees around the stem.

16. The medical device of claim 15, wherein the motor assembly is connected to a top of the stem.

17. The medical device of claim 16, wherein the stabilization leg is configured to extend through the caster to the contact surface.

18. The medical device of claim 12, wherein the motor assembly further comprises a motor, a motor cover that encloses each motor, a motor cap disposed on top of each motor, and a motor bracket that supports each motor.

* * * * *